US00PP19685P2

(12) United States Plant Patent
Lamb et al.

(10) Patent No.: US PP19,685 P2
(45) Date of Patent: Feb. 10, 2009

(54) ***ANTHURIUM* PLANT NAMED 'TWYANAG2'**

(50) Latin Name: *Anthurium hybrida*
Varietal Denomination: TWYANAG2

(75) Inventors: Ann E. Lamb, Sebring, FL (US); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/906,561

(22) Filed: Oct. 3, 2007

(51) Int. Cl.
*A01H 5/00* (2006.01)

(52) U.S. Cl. ..... Plt./365

(58) Field of Classification Search ..... Plt./365
See application file for complete search history.

*Primary Examiner*—Annette H Para
*Assistant Examiner*—S. B. McCormick Ewoldt
(74) *Attorney, Agent, or Firm*—Jondle & Associates, P.C.

(57) ABSTRACT

A new *Anthurium* plant particularly distinguished by having numerous, large, shiny, bright-orange spathes, numerous dark-green, durable, shiny leaves, an upright growth habit and by being easy to grow, is disclosed.

1 Drawing Sheet

Genus and species: *Anthurium hybrida.*
Variety denomination: 'TWYANAG2'.

BACKGROUND OF THE NEW PLANT

The present invention comprises a new and distinct cultivar of *Anthurium,* botanically known as *Anthurium hybrida,* and hereinafter referred to by the cultivar name 'TWYANAG2'. The new cultivar originated from a hybridization made in winter 2004 in Apopka, Fla., USA. The female parent was the proprietary *Anthurium* plant 'Orange Cup' (unpatented), while the male parent was the *Anthurium* plant 'Orange Crush' (U.S. Plant Pat. No. 12,316). The first propagation was done in the Summer of 2004.

The new cultivar was selected in March 2005 from the results of the hybridization and has been asexually reproduced repeatedly by tissue culture in Apopka, Fla., USA for approximately two and one-half years. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1) Numerous, large, shiny, bright-orange spathes;
2) Numerous, dark-green, durable, shiny leaves;
3) Upright growth habit; and
4) Easy to grow.

DESCRIPTION OF PHOTOGRAPH

This new *Anthurium* plant is illustrated by the accompanying photograph which shows the overall plant habit including blooms, buds and foliage of the plant. The colors shown are as true as can be reasonably obtained by conventional photographic procedures. The photograph is of a 24 month old plant grown in a greenhouse in Apopka, Fla.

DESCRIPTION OF THE NEW CULTIVAR

The following detailed description sets forth the distinctive characteristics of 'TWYANAG2'. The data which define these characteristics were collected from asexual reproductions carried out in Apopka, Fla. The plant history was taken on 24 month old plants which were planted from tissue culture in 25-cm pots and grown in a greenhouse with average daily temperatures of 85° F.–95° F. and average nightly temperatures of 72° F. to 78° F. Observations were made in March 2007. Color readings were taken under natural light in the greenhouse. Color references are primarily to the R.H.S. Colour Chart of The Royal Horticultural Society of London (R.H.S.) (2001).

DETAILED BOTANICAL DESCRIPTION

Classification:
- *Family.*—Aracea.
- *Botanical.*—*Anthurium hybrida.*
- *Common.*—*Anthurium.*

Parentage:
- *Female parent.*—*Anthurium* plant 'Orange Cup' (unpatented) with light-orange cupped spathes.
- *Male parent.*—*Anthurium* plant 'Orange Crush' (U.S. Pat. No. 12,316) with red-orange spathes.

Growth:
- *Form.*—Upright, symmetrical, inverted triangle with outward pointed leaves; plant wider than tall.
- *Growth and branching habit.*—Upright stems, branched habit (basal, axillary branching), with many leaves and flowers; vigorous growth habit, plant produces numerous branches, leaves and flowers.
- *Height* (*measured from soil to top of canopy*).—43 cm to 48 cm.
- *Height* (*measured from soil to top of inflorescences*).—52 cm to 62 cm (flowers at, among and above the top of the foliage).
- *Width* (*area of spread*).—70 cm to 78 cm.
- *Time to produce a finished flowering plant.*—Single micro cutting to liner: 14 to 16 weeks. 10 cm pot from liner: 7 to 8 months (first flowers). 15 cm pot from liner: 10 to 12 months. 20 cm pot from liner: 14 months.

*Growth rate.*—Typical of commercial *Anthurium* cultivars.

*Root description.*—Thick fleshy roots with finer laterals; RHS 199D and RHS 180D (greenish-grey); RHS 179A where exposed to light; RHS 154B root tips.

*Durability of foliage to stresses.*—Durable, holds up well under typical commercial practice.

*High temperature tolerance.*—To about 104° F. without damage.

*Low temperature tolerance.*—To about 55° F. without damage.

Stems:

*Number of stems per plant.*—9.

*Length (from soil line to the junction of the last two unrolled leaves).*—17 cm.

*Diameter (measured from about 8 cm above the soil surface).*—1.3 cm.

*Internode length.*—1.7 cm to 2.5 cm.

*Color.*—Immature: Between RHS 145A to RHS 145B sheathed with green cataphylls tinged with bronze. Mature: Between RHS 146C to RHS 146D sheathed with dried cataphylls between RHS N199B to RHS N199C (brown).

*Appearance (shape).*—Upright, cylindrical, round, thick with regularly spaced petioles and short internodes; cataphylls are present and nonpersistant; surface is smooth and glossy.

*Pubescence.*—Absent.

*Aspect.*—Upright.

*Strength.*—Sturdy, tough, upright.

*Cataphylls.*—Shape and arrangement: Lanceolate, mucronate, acute, one or two keeled; base of cataphyll clasps the stem. Length: 7.0 cm to 12.0 cm. Width: 3.8 cm (flattened). Texture: Inside: Shiny, smooth. Outside: Glossy. Color: Between RHS 145A to RHS 145B; RHS 144C often tinged with RHS 166C; becoming between RHS N199B to RHS N199C with senescence.

Leaves:

*Arrangement and type.*—Alternate, simple, single leaf per petiole; midrib on lower surface is keeled.

*Quantity of leaves per stem.*—6 per main stem; fewer leaves on younger axillary branches.

*Length.*—16 cm to 19 cm.

*Width (natural).*—11 cm to 15 cm.

*Width (flattened).*—12 cm to 16 cm.

*Shape.*—Ovate; leaf blade folded upward lengthwise.

*Apex.*—Acuminate, mucronate.

*Base.*—Cordate.

*Margin.*—Entire, with some broad undulations; leaf blade folded upward lengthwise.

*Appearance (on both surfaces).*—Smooth, medium thickness, rigid, firm/leathery, shiny, dulling with age.

*Pubescence (on both surfaces).*—Absent.

*Immature leaf color.*—Upper surface (newly emerged): Between RHS 146A to RHS 147A and tinged with RHS 165A. Upper surface (fully emerged): Darker than, but closest to between RHS 146A to RHS 147A. Lower surface (newly emerged): RHS 147B and tinged with RHS 177C. Lower surface (fully emerged): Between RHS 146A to RHS 146B tinged with RHS 173B.

*Mature leaf color.*—Upper surface: Between RHS 147A to RHS N189A. Lower surface: Between RHS 146A to RHS 146B.

*Venation.*—Pinnate. Venation color: Upper surface: Immature: RHS 146C tinged with RHS 165B. Immature midrib: RHS 146C tinged with RHS 165B. Mature: RHS 146C. Mature midrib: RHS 146C. Lower surface: Immature: RHS 144C tinged with colors between RHS 177C to RHS 177D. Immature midrib: RHS 144C tinged with RHS 177C. Mature: Between RHS 144B to RHS 144C. Mature midrib: RHS 144C.

*Petiole.*—Aspect: Vertical and upright when newly emerged, becoming about 30° from the vertical axis with maturity. Length (from base of leaf to junction of petiole and stem): 36 cm. Diameter: Distal (measured in the center below the geniculum and above the petiole wing tip): 0.40 cm. Proximal: 0.14 cm. Color: Immature: Between RHS 175A to RHS 164A. Mature: RHS 146C.

*Geniculum.*—Length: 2.1 cm. Diameter: 0.45 cm. Aspect: Straight or curved upward. Color: RHS 146C often tinged with RHS 183A.

*Wing.*—Length: 5.0 cm (tip of wing flush with petiole). Diameter: 0.8 cm. Color: Between RHS 144B to RHS 144C.

Inflorescence:

*Arrangement.*—Spathe/spadix atop peduncle, emerges from petiole sheath; peduncle attached to stem at leaf axil; inflorescences mostly clustered along the center of the plant; persistent.

*Aspect.*—Upright straight, vertical when newly emerged, leaning outward to about 30° with age.

*Height.*—52 cm to 62 cm.

*Depth.*—Spathe nearly flat, or cupped upward 1.0 cm deep.

*Flowering habit and season.*—Continuous flowering year round, but most prolific in winter and spring.

*Number of inflorescences per plant.*—20 inflorescences and buds.

*Buds.*—Shape is lanceolate, straight and with the distal end curved downward, length is 5.8 cm to 7.9 cm, width is 0.85 cm to 1.1 cm and color is RHS 41A while the apex is tinged with RHS 154D.

*Fragrance.*—Absent.

*Rate of inflorescence opening.*—About every 14 days, 2 to 3 new inflorescences emerge.

*Longevity on plant.*—8 weeks.

*Longevity as cut flower.*—3 to 4 weeks.

Spathe:

*Appearance.*—Medium sized, heart-shaped, bright-orange, margins slightly cupped upward, apex often curves downward; glossy, medium thickness, firm/leathery, slightly concave between veins.

*Arrangement/aspect.*—Variable; typically horizontal or about 45° from the vertical.

*Pubescence (on both surfaces).*—Absent.

*Shape.*—Ovate with cordate base.

*Margin.*—Entire, mostly smooth with some broad undulations.

*Apex.*—Acuminate, mucronate.

*Base.*—Cordate.

*Longevity.*—8 weeks with good color.

*Size.*—Length: 7.0 cm to 10 cm. Width (natural): 5.0 cm to 7.5 cm. Width (flattened): 6.2 cm to 8.3 cm.

*Color.*—When opening: Front side: RHS 44C. Rear side: RHS 39A. Fully opened: Front side: RHS 41A. Rear side: Between RHS 39A to RHS 39B. Fading to: Between RHS N34A to RHS 34A to RHS 34B, variably tinged with colors between RHS 146A to RHS 146B (green).

Spadix:

*Appearance.*—Columnar, upright, affixed atop very short stipe at junction of peduncle and spathe.

*Arrangement/aspect.*—Upright, near vertical, or tilted outward.

*Shape.*—Columnar, narrower, tapered at tip; apex bluntly rounded.

*Margin.*—Round in transverse section.

*Apex.*—Bluntly rounded, obtuse.

*Base.*—Bluntly rounded, terminates atop a short stipe.

*Size.*—Length: 5.3 cm to 6.0 cm. Diameter: 0.7 cm.

*Color* (*immature*).—Proximal: Between RHS 186A to RHS 186B. Distal: RHS 34A.

*Color* (*mature*).—RHS 184C.

Flowers:

*Arrangement.*—Flowers reduced, tightly packed on spadix.

*Type.*—Bisexual, reduced, minuscule; female flowers receptive first, followed by male flowers.

*Shape.*—Individual flowers roughly pyramidal in shape, tightly packed on the spadix; flowers nearly sessile on spadix; face of individual flower flat and square or diamond shaped; pistil in center, protruding, surrounded by anthers; four triangular tepals at corners.

*Diameter.*—0.22 cm.

*Height.*—0.27 cm from base to tip of pistil; stigma protrudes about 0.08 cm when receptive.

*Number of female flowers per spadix.*—180.

*Number of male anthers per flower.*—About 8 (minuscule; not clearly visible).

Peduncle:

*Length.*—40 cm.

*Diameter.*—0.40 cm.

*Angle.*—Straight, upright or slightly outward leaning.

*Strength.*—Sturdy, somewhat flexible.

*Color.*—Proximal: RHS 146B tinged with RHS 175B. Distal: RHS 175B.

Pedicel:

*Length* (*stipe*).—0.4 cm, stipe reduced, flowers nearly sessile.

*Diameter* (*stipe*).—0.6 cm.

*Angle.*—Straight, upright.

*Strength.*—Sturdy.

*Color.*—RHS 39B.

Reproductive organs:

*Anther color.*—Same as surrounding spadix tissue.

*Pollen amount.*—Sparse.

*Pollen color.*—RHS 155D (white).

*Stigma color.*—RHS 186D.

*Ovary color.*—RHS 155C.

Fruit and seed set: Seed production has not been observed to date.

Disease and insect resistance: No particular resistance or susceptibility different from other *Anthurium* varieties.

COMPARISON WITH PARENTAL AND COMMERCIAL CULTIVARS

'TWYANAG2' differs from the female parent *Anthurium* plant 'Orange Cup' (unpatented), by having smaller, flatter, more numerous, bright-orange spathes and a purple spadix tinged with orange, while 'Orange Cup' has larger, lighter-orange, cupped spathes and a yellow-white spadix. 'TWYANAG2' has a larger, more upright growth habit, while 'Orange Cup' has a shorter, more compact growth habit. In addition, 'TWYANAG2' has darker-green, more durable and shinier leaves as well as immature leaves that are tinged with bronze, while 'Orange Cup' has leaves that are entirely lighter green and are prone to yellowing at high temperatures.

'TWYANAG2' differs from the male parent *Anthurium* plant 'Orange Crush' (U.S. Plant Pat. No. 12,316) by having smaller, flatter, more numerous bright orange spathes and inflorescences that are mostly clustered in the center of the plant and sit among or above the foliage, while 'Orange Crush' has slightly larger, fewer spathes that are more red-orange in color and inflorescences that are more outward leaning and sit higher above the foliage. In addition, 'TWYANAG2' has a larger more upright plant habit, while 'Orange Crush' has a shorter more compact plant habit.

'TWYANAG2' differs from the commercial variety 'Orange Hot' (unpatented), by having larger, longer lasting, bright-orange spathes, while 'Orange Hot' has smaller, pale-orange spathes that are less durable. 'TWYANAG2' has smaller leaves than 'Orange Hot'. In addition, 'TWYANAG2' has a more prolific bloom than 'Orange Hot'.

I claim:

1. A new and distinct cultivar of *anthurium* plant as shown and described herein.

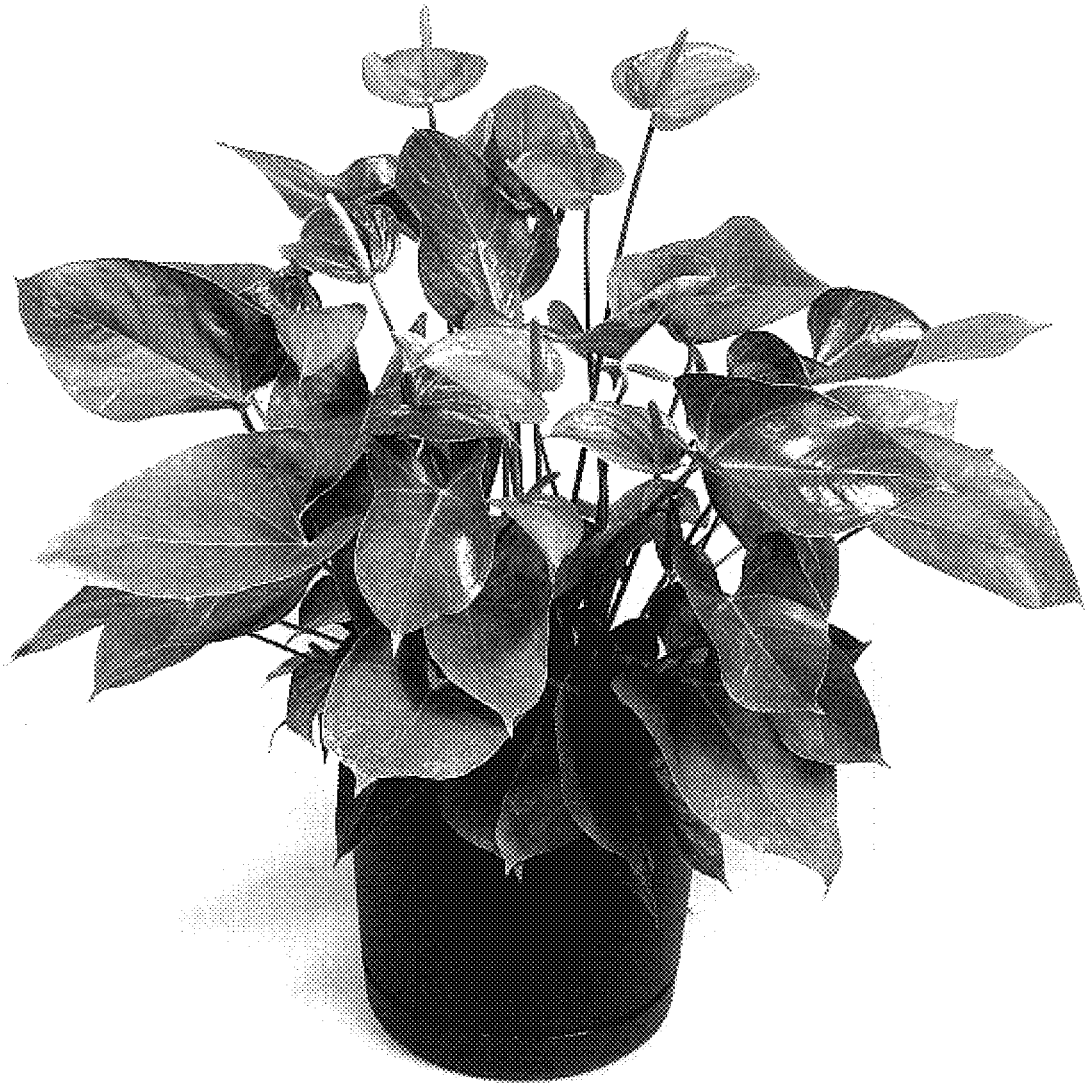

* * * * *